United States Patent
Levy et al.

(10) Patent No.: US 7,838,742 B2
(45) Date of Patent: Nov. 23, 2010

(54) PEPPER PLANTS HAVING FRUIT WITH ALTERED VITAMIN CONTENT

(75) Inventors: Arieh Levy, Rehovot (IL); Nissim Yonash, Gan Yavne (IL); Alon Haberfeld, Mazkeret Batia (IL); Serge Benarous, Kiryat Gat (IL); Joseph Kanner, Rehovot (IL); Rina Granit, Rehovot (IL); Ezra Menagem, Rehovot (IL); Michal Barzilai, Rehovot (IL)

(73) Assignees: Hazera Genetics Ltd., M.P. Shikmim (IL); State of Israel, Ministry of Agriculture, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 11/909,153

(22) PCT Filed: Mar. 22, 2006

(86) PCT No.: PCT/IL2006/000371

§ 371 (c)(1),
(2), (4) Date: Sep. 19, 2007

(87) PCT Pub. No.: WO2006/100680

PCT Pub. Date: Sep. 28, 2006

(65) Prior Publication Data

US 2008/0209584 A1    Aug. 28, 2008

Related U.S. Application Data

(60) Provisional application No. 60/663,878, filed on Mar. 22, 2005.

(51) Int. Cl.
*A01H 5/00* (2006.01)
*A01H 1/00* (2006.01)
*A01H 4/00* (2006.01)
*C12N 15/82* (2006.01)

(52) U.S. Cl. .................. 800/317; 800/260; 435/410

(58) Field of Classification Search ............. 800/317.1, 800/260; 435/410
See application file for complete search history.

(56) References Cited

U.S. PATENT DOCUMENTS 6,670,530 B2 * 12/2003 Eby et al. .............. 800/312

OTHER PUBLICATIONS

Gnayfeed et al. Content of bioactive compounds in pungent spice red pepper (paprika) as affected by ripening and genotype. (2001) J. of the Sci. and FOod and Agric. vol. 81, pp. 1580-1585.*
Poehlman et al. 1995. Breeding Field Crops, 4th ed., p. 108.*
Daood et al. 1996. Food Chemistry 55(4): 365-372.*
Dawson et al., 1969. Data for Biochemical Research, Clarendon Press, Oxford, England p. 329.
Levy et al. "Carotenoid Pigments and .beta.-Carotene in Paprika Fruits (*Capsicum* spp.) with Different Genotypes", J. Agric. Food Chem.; 1995; 43(2); 362-366.
Meydani et al., "Assessment of the safety of supplementation with different amounts of vitamin E in healthy older adults", Am J Clin Nutr. Aug. 1998;68(2):311-8.
Rimm et al., "Vitamin E Consumption and the Risk of Coronary Heart Disease in Men", N. Engl J Med. May 20, 1993;328(20):1450-6.
Stewart et al., "The Pun1 gene for pungency in pepper encodes a putative acyltransferase", Plant J. Jun. 2005;42(5):675-88.
Bosland et al., "'NuMex Sunrise', 'NuMex Sunset', and 'NuMex Eclipse' Ornamental Chile Peppers", *Hortscience*, 25(7):820-821 (1990).
International Search Report for PCT/IL2006/000371 dated Aug. 25, 2008 (3 pages).
Written Opinion of the International Searching Authority for PCT/IL2006/000371 dated Aug. 25, 2008 (4 pages).

* cited by examiner

*Primary Examiner*—David H Kruse
*Assistant Examiner*—Keith O. Robinson
(74) *Attorney, Agent, or Firm*—Fennemore Craig, P.C.

(57) ABSTRACT

The present invention provides pepper plants having edible fruit with altered vitamin content, specifically fruit comprising an elevated content of vitamin E, further comprising at least one of an elevated content of pro-vitamin A, an elevated content of vitamin C and combinations thereof. The concentration of vitamin E is at least 5 mg/100 g fresh weight, and the plants are selected to be lacking molecular markers linked to undesirable traits.

23 Claims, 4 Drawing Sheets

CLR-7174  X C-8271

High Pro-Vitamin A
•Thin pericarp

High Vitamin C
•Pungent fruit

Maor  X E-8511

High Vitamin E
•Pungent fruit
•Thin pericarp

F1 X F1

F2  5,500 Plants

Selection of 300 plant with desirable horticulture traits

Selection of plants having fruit with high vitamin E and at least one of pro-vitamin A and vitamin C, non-pungent and with thick pericarp

PEPPER PLANTS HAVING FRUIT WITH ALTERED VITAMIN CONTENT

RELATED APPLICATION DATA

This application is the U.S. national stage of PCT/IL2006/000371 filed on Mar. 22, 2006, which is based on and claims the benefit of U.S. Provisional Patent Application No. 60/663,878 filed on Mar. 22, 2005, the content of each of which is expressly incorporated herein in its entirety by this reference.

FIELD OF THE INVENTION

The present invention relates to pepper plants having fruit with altered vitamin content, specifically fresh edible fruit with an elevated content of vitamin E and at least one of an elevated pro-vitamin A content, an elevated vitamin C content and combinations thereof. The invention further relates to plants selected to be lacking genetic markers linked to undesirable traits, while possessing the desired traits of elevated vitamin content.

BACKGROUND OF THE INVENTION

Natural vitamins are organic food substances essential for the normal function of the mammal body. However, with few exceptions, mammals cannot manufacture or synthesize vitamins, and, consequently, vitamins must be supplied in the diet or as nutritional supplements. The amount of a certain vitamin that should be consumed depends on age, gender and type of vitamin. The Recommended Dietary Allowance (RDA) of a vitamin is the average daily dietary intake level that is sufficient to meet the nutrient requirement of nearly all (97-98%) healthy individuals in each life-stage and gender group. It is not recommended to consume vitamins at doses over the RDA, as high concentration of certain vitamins may cause health problems. Upper tolerable levels of a vitamin are typically identified as the level which "represents the maximum intake of nutrient that is likely to pose no risk of adverse health effects in almost all individuals in the general population" (Institute of Medicine, Food and Nutrition board. Dietary Reference Intakes: Vitamin C, Vitamin E, Selenium, and Carotenoids. National Academy Press, Washington, D.C., 2000).

For humans, fruit and vegetables are the main dietary source of vitamins, including the anti-oxidative vitamins vitamin E, vitamin A and vitamin C.

Tocopherol compounds, also called vitamin E, are active components found in vegetable oils. Vitamin E exists in eight different chemical forms, of which the most effective form in humans is α-tocopherol. Vitamin E activity refers to the physiological activity of this group of nutrient materials. Materials having a vitamin E activity are all derivatives of chroman-6-ol. These compounds are tocol derivatives having an isoprenoid $C_{16}$-sidechain. The term "tocol" refers to 2-methyl-2-(4',8',12'-trimethyltridecyl)chroman-6-ol. These compounds, which include alpha-, beta-, gamma-, and delta-tocopherol, are of primary importance for vitamin E activity.

Recently published prospective health studies demonstrate that vitamin E supplement ingestion is associated with a reduced risk of coronary heart disease (CHD) in both women and men. For example, Rimm et al., (NEJM, 328, 1450-1456, 1993) showed that the risk of CHD diminished significantly as the daily supplemental level of vitamin E increased. This study indicates that the current RDA of 15-25 international units (IU) of vitamin E (i.e. 10-15 mg/day) may not be sufficient for obtaining the full protective benefits of vitamin E. Other studies have shown the beneficial function of vitamin E for protecting plasma LDL cholesterol and cellular components against oxidative damage, and for maintaining normal immunological function to protect the body against diseases. It has also been shown in a subject study, based upon an extensive battery of blood tests, that even high daily doses of vitamin E ingested by healthy elderly people for extended periods of time (i.e., 800 IU per day for 4 months), caused no side-effects, and no negative changes in general health or metabolic functions (Meydani et al., Am. J. Clin. Nutr. 68: 311-318, 1998). In contrast, significant improvements in T cell mediated function and significant increases in plasma vitamin E levels were noted. Vegetables oils, nuts, and green leafy vegetables are good sources of vitamin E. However, the amount of vitamin E provided by one serving of, for example, Mango fruit or Broccoli provides only about 5-8 percent of the recommended daily amount.

From the family of vitamin A compounds, retinol is the most active, or usable form, which can be converted to retinal and retinoic acid, other active forms of vitamin A. Carotenoids are a family of pigments that give fruit their yellow to red color. Of the pro-vitamin A carotenoids, β-carotene is more efficiently converted to retinol than other pro-vitamin carotenoids, for example α-carotene and β-cryptoxanthin. Other known carotenoids, such as lycopene, lutein and zeaxanthin are not sources of vitamin A, however, they are also important nutrients having potent anti-oxidative properties as well as anti-carcinogenic activity. Vitamin A plays an important role in bone growth, cell division and cell differentiation. Vitamin A, specifically retinol, is involved in maintaining the surface linings of the eyes, respiratory, urinary and intestinal tracts and as such has a role in preventing infection by maintaining those linings intact. Vitamin A is recently used for maintaining the integrity of the skin and mucous membranes and preventing bacterial and viral infection. It is also known to help regulate the immune system. The RDA for vitamin A is listed as Retinol Activity Equivalents (RAE) to account for the different activities of retinol and pro-vitamin A carotenoids and is currently 600-900 µg depending on age and gender. High storage levels of vitamin A in the body (hypervitaminosis A) can lead to toxic symptoms. There are three major adverse effects resulting from overdose of vitamin A: birth defects, liver abnormalities, and reduced bone mineral density that may result in osteoporosis. Toxic symptoms can also arise after consuming very large amounts of preformed vitamin A over a short period of time. Vitamin A is found in animal food products, such as liver, whole milk and whole eggs. However, high consumption of such food products is not recommended due to high content of fat and cholesterol. Consuming darkly colored vegetables and fruit containing β-carotene is therefore preferable. Moreover, the conversion of pro-vitamin A carotenoids to vitamin A decreases when body stores are full, which naturally limits further increases in storage levels and prevents hypervitaminosis A.

Vitamin C, also known as ascorbic acid, is essential for proper nutrition for various reasons, including but not limited to its role as an antioxidant. Many nutritional substances are destroyed by oxidation, but vitamin C, by becoming oxidized itself, can protect these substances (Understanding Nutrition, 294, Whitney and Rolfes Eds. 6th Ed., 1993). Food manufacturers will often add vitamin C to their products to protect the food from oxidation. Inside the body, vitamin C protects other vitamins and minerals from oxidation. For example, in the intestines, vitamin C protects iron and thus promotes its bioavailability.

Vitamin C participates in the formation of collagen, the fibrous, structural protein that comprises connective tissue, and in the metabolism of several amino acids, including amino acids which are converted into the hormones epinephrine and thyroxin. Exposure to colds and infection increases the need for vitamin C. Thyroxin, made with vitamin C, regulates the metabolic rate, which increases whenever the body needs to produce heat, for example during a fever or in very cold weather.

Different countries set different daily requirements for vitamin C, but most agree that about 10 mg each day will present vitamin C deficiency (scurvy). At 60 mg per day, the body will stop responding to further vitamin C intake. At 100 mg each day, all of the body's tissues are saturated, and the body will begin to excrete excess vitamin C. The Recommended Daily Allowance (RDA) of vitamin C in the United States is 60 mg per day. However, more vitamin C may be indicated if the patient has just gone through some physiological or psychological stress, consumes alcohol daily or smokes. Pregnant or breast-feeding women also require additional vitamin C, due to the portion of their daily intake that goes to the fetus or breast milk.

An excess vitamin C can be toxic, causing cramps, nausea and diarrhea and can also obscure the presence of diabetes. Toxic levels can start at 2 g a day. Good sources of vitamin C include citrus fruits, broccoli, cauliflower, strawberries, potatoes and organ meats such as kidney and liver.

In summary, obtaining vitamin A, C and E in the diet is necessary for keeping good health, and fruit and vegetables are preferable sources of these vitamins.

Pepper belongs to the genus *Capsicum*, which includes the species *Capsicum annum* and *Capsicum frutescens* from which most cultivated peppers are derived. Peppers are cultivated and used around the world as sweet peppers, such as the bell pepper; as pungent chili peppers, such as jalapeno peppers, as TABASCO peppers (used to make TABASCO sauce); and as a source of dried powders of various colors such as paprika. Pepper fruit, specifically those having red and orange-colored fruit are known as a source for carotenoids, including pro-vitamin A carotenoids. Vitamin C may be also present in sufficient amount, but fruit containing high vitamin C content are typically pungent. In pepper varieties having edible fruit the vitamin E content provides only for a low portion of the RDA per serving. High vitamin content is typically linked to pungent fruit having a thin pericarp, which is the edible part of pepper fruit. Such pungent fruit are freshly consumed as spices at small serving size, which dramatically reduces the vitamin content that may be consumed. The traits of pungency and thin pericarp, which are undesirable edible fruit, are difficult to remove by breeding and it is therefore expected that the development of plant capable of producing fruit having high vitamin E content at a commercial level from the pungent varieties would be lengthy and difficult.

Thus, it would be highly advantageous to have a pepper plant having fruit with elevated content of Vitamin E, and at least one of pro-vitamin A, vitamin C, while being devoid of pungency and other undesirable traits.

SUMMARY OF THE INVENTION

The present invention addresses the need for pepper fruit with improved vitamin content. Accordingly, the present invention provides a pepper plant suitable for commercial growth having edible sweet fruit with altered vitamin content as compared with the edible fruit of currently available commercial pepper strains. More specifically, the present invention provides a pepper plant having fruit with altered vitamin content as compared with the currently available commercial pepper strains, the fruit comprising an elevated vitamin E content, and further comprising at least one of an elevated pro-vitamin A content, an elevated vitamin C content or a combination thereof, wherein the vitamin E concentration is at least 5 mg/100 g fresh weight (FW). The fruit of the present invention are also selected to be non-pungent and to have a thick pericarp. Such selection is achieved, for example, using DNA markers.

Preferably, the pepper fruit comprise an elevated content of all three essential vitamins, wherein the concentration of pro-vitamin A is at least about 3 mg/100 g FW and that of vitamin C is at least about 200 mg/100 g FW, preferably in the range of from about 200 mg/100 gFW to about 500 mg/100 g FW. Further preferably, the pepper fruit comprise elevated content of total carotenoids of at least 70 mg/100 g FW. The plants of the invention can be in the form of stable true-breeding lines, or as a more diverse material including hybrids, crosses and the like, all of which provide fruit with altered vitamin content, as described above.

The present invention further relates to seeds of the plants of the present invention, to plants grown from the seeds, to their progeny, to fruit produced by the plants, to plant parts derived therefrom and to methods of producing same. The present invention also relates to products obtained from the superior, high vitamin pepper fruit produced by the plants of the present invention.

According to one aspect, the present invention provides a pepper plant having fruit with altered vitamin content as compared with edible fruit of currently available commercial pepper strains, the fruit comprising an elevated vitamin E content, further comprising at least one of an elevated pro-vitamin A content, an elevated vitamin C content and a combination thereof, wherein the concentration of vitamin E is at least about 5 mg/100 g FW. According to certain embodiments, the fruit are non-pungent and have a thick pericarp.

According to one embodiment, the fruit comprise at least about 7 mg/100 g FW Vitamin E, preferably at least about 9 mg/100 g FW, more preferably at least about 11 mg/100 g FW vitamin E.

According to another embodiment, the present invention provides a pepper plant having fruit comprising at least about 5 mg/100 g FW vitamin E, further comprising pro-vitamin A. According to yet another embodiment, the present invention provides a pepper plant having fruit comprising at least about 5 mg/100 g FW vitamin E, further comprising Vitamin C. According to a further embodiment, the present invention provides a pepper plant having fruit comprising at least about 5 mg/100 g FW vitamin E, further comprising an elevated content of pro-vitamin A and vitamin C. According to certain embodiments, the fruit are non-pungent and have a thick pericarp.

According to one embodiment, the pro-vitamin A concentration is at least about 3 mg/100 g FW, preferably at least about 4 mg/100 FW, more preferably at least about 6 mg/100 g FW, and the vitamin C concentration is at least about 200 mg/100 g FW, preferably in the range of from about 200 mg/100 g FW to about 500 mg/100 g FW.

According to a still further embodiment, the fruit produced by the pepper plant of the present invention further comprise an elevated content of total carotenoids. According to one embodiment, the total carotenoids concentration is at least about 70 mg/100 g FW.

As used herein, the term "altered vitamin content" refers to elevated vitamin E concentration and an elevated concentration of at least one of pro-vitamin A and vitamin C as described above, and combinations thereof, which are altered compared to hitherto known vitamin concentration in pepper fruit, particularly currently available commercial fresh edible pepper fruit which are non-pungent and have a thick pericarp. The known vitamin concentration in such edible pepper fruit is vitamin E concentration of about 1.5-3.0 mg/100 g FW; pro-vitamin A of about 11.0 mg/100 g FW; and vitamin C of about 100 mg/100 g FW. In a preferred embodiment, the concentration(s) of vitamin E, pro-vitamin A and/or vitamin C is/are elevated as compared with the concentrations of vitamin E, pro-vitamin A and/or vitamin C found in currently available commercial edible pepper fruit.

As described hereinabove, natural sources for vitamin E contain only a low proportion of the vitamin required daily dose. Fruit are not included in the known sources for higher amount of vitamin E, such sources being typically high in calories and therefore less recommended for a healthy diet. As of today, obtaining the required amount of vitamin E requires consumption of food fortified with synthetic α-tocopherol, which is not identical to the natural form and is less active compared to the natural form.

Hitherto, an elevated concentration of vitamin C and vitamin E was found only in pungent pepper fruit and paprika-type fruit, respectively, which may be served only at small size servings or that are not typically consumed as fresh produce, thus providing only small proportion of the RDA.

The present invention answers these limitations, by providing a pepper plant having edible pepper fruit for fresh produce, the fruit comprising elevated concentrations of vitamin E, and further comprising elevated concentrations of at least one of pro-vitamin A, specifically β-carotene, and the anti-oxidative vitamin C, as compared with the concentrations of these vitamins found in currently available commercial pepper fruit. Preferably, the fruit also comprise an elevated content of total carotenoids.

According to certain embodiments, the present invention provides pepper plants lacking a DNA sequence, which co-segregates with a high pungency trait. According to one embodiment, the DNA sequence is a template for amplification of a DNA fragment, wherein the DNA fragment is used as a molecular marker for pungency, such that plants lacking the DNA marker are non-pungent. According to one embodiment, the DNA sequence co-segregating with a high pungency comprises a polynucleotide sequence as set forth in SEQ ID NO:3 or a fragment thereof. According to one currently preferred embodiment, the DNA sequence co-segregating with pungency is a template for amplification of a DNA fragment using a first primer having a polynucleotide sequence as set forth in SEQ ID NO:1 and a second primer having a polynucleotide sequence as set forth in SEQ ID NO:2. The resulted DNA fragment is of about 700 bp, having the nucleotide sequence set forth in SEQ ID NO:3. Thus, according to one currently preferred embodiment, the plants of the present invention are lacking a DNA fragment having sequence ID NO:3.

According to some embodiments, the plants of the present invention produce fruit having an average weight of 100 g. The RDA of vitamin E is, as of today, 10-15 mg. Therefore, a single 100 g pepper fruit of the present invention contain at least 25% of the RDA of vitamin E, preferably up to 55% of the RDA, which is about three to five fold the vitamin E amount provided by currently available commercially produced sweet pepper fruit. As the fruit of the present invention are devoid of pungency, a serving size is at least one fruit of about 100 g.

According to another aspect, the present invention provides pepper plants that yield fruit crops with altered vitamin content comprising an elevated vitamin E content, further comprising at least one of an elevated pro-vitamin A content, an elevated vitamin C content or a combination thereof, wherein the average crop concentration of vitamin E is at least 5 mg/100 g FW. According to certain embodiments, the fruit are non-pungent and have a thick pericarp.

Pepper plants within the scope of the present invention encompass any plant having edible pepper fruit with altered vitamin content comprising an elevated vitamin E content, further comprising at least one of an elevated pro-vitamin A content, an elevated vitamin C content and combinations thereof, wherein the vitamin E concentration is at least about 5 mg/100 g FW. The fresh, edible pepper fruit are devoid of pungency and have a thick pericarp. The pepper plants advantageously can further comprise beneficial agronomical traits as are well known in the art including but not limited to high germination rate, herbicide resistance, insect resistance, resistance to bacterial, fungal or viral diseases, resistance to various types of non-biotic stress, male sterility and vigorous growth.

The plants of the invention are preferably non-genetically modified (non-GMO); however it is to be understood that the addition or deletion of traits by transformation is explicitly encompassed within the scope of the invention.

The present invention also provides seeds of pepper wherein the plants grown from the seeds have edible fruit with altered vitamin content, specifically an elevated vitamin E content, and at least one of an elevated pro-vitamin A content, an elevated vitamin C content or a combinations thereof, as described herein above. According to certain embodiments, the fruit of the plants grown from the seeds are non-pungent and have a thick pericarp.

The pepper plants grown from the seeds of the present invention can be in the form of a stable true-breeding line or as a more diverse material, all of which having edible pepper fruit with altered vitamin content as described herein above.

*Capsicum annuum* hybrid ACE05F01-521 serves as an example for the plants of the present invention. Representative seeds of ACE05F01-521 were deposited with NCIMB Ltd. on Mar. 9, 2006 under Accession Number 41381. An additional amount of ACE05F01-521 seeds were deposited with NCIMB Ltd. on Jun. 3, 2010 under Accession Number 41722. Plants grown from seeds of ACE05F01-521 produce edible fruit with elevated vitamin content according to the teaching of the present invention as described herein below.

Pollen and ovules from the pepper plants of the present invention; the seeds produced from same and the plants grown from the seeds and fruit produced by these plants; are also encompassed within the scope of the present invention.

According to yet another aspect, the present invention provides a tissue culture regenerated from the plants of the present invention and plants regenerated therefrom.

According to one embodiment, the tissue culture comprises cells or protoplasts derived from a tissue selected from the group consisting of, but not limited to, leaves, pollen, embryos, roots, root tips, anthers, flowers, fruit and seeds.

According to yet further aspect, the present invention provides an edible pepper fruit with altered vitamin content compared to currently available sweet edible pepper fruit as described herein above. According to certain embodiments, the fruit are non-pungent and have a thick pericarp. The fresh fruit can be marketed as a fresh produce or can serve as a source for processed pepper products.

According to yet another aspect, the present invention provides a method for producing pepper plants having edible fruit with altered vitamin content, comprising the steps of: selecting at least one pepper plant having fruit comprising an elevated vitamin E content, at least one pepper plant having fruit comprising an elevated pro-vitamin A content and at least one pepper plant having fruit comprising an elevated vitamin C content as compared with the edible fruit of currently available commercial pepper strains; crossing each of the high vitamin content plants with a known commercial plant as to produce at least one population; screening the population for plants devoid of the linkage between high vitamin content and pungency using a DNA marker and between high vitamin content and thin pericarp; and selecting plants with pepper fruit having vitamin E concentration of at least about 5 mg/100 g FW and at least one of pro-vitamin A concentration of at least about 3 mg/100 g FW and vitamin C concentration in the range of from about 200 mg/100 g FW to about 500 mg/100 g FW or a combination thereof, being non-pungent and having thick pericarp.

According to one embodiment, the method comprises the steps of: selecting at least one pepper plant having fruit comprising an elevated vitamin E content, at least one pepper plant having fruit comprising an elevated pro-vitamin A content and at least one pepper plant having fruit comprising an elevated vitamin C content as compared with edible fruit of currently available commercial pepper strains; crossing the at least one pepper plant having fruit comprising an elevated vitamin E content with a known commercial plant to produce a first $F_1$ population; crossing the at least one pepper plant having fruit comprising an elevated pro-vitamin A content with the at least one pepper plant having fruit comprising an elevated vitamin C content to produce a second $F_1$ population; collecting the seeds of the first and the second $F_1$ populations; growing plants from said first and said second $F_1$ seed populations; crossing at least one plant from said first $F_1$ population with at least one plant from said second $F_1$ population to produce $F_2$ population; collecting the hybrid $F_2$ seeds; growing $F_2$ plants from the $F_2$ seeds; examining the presence of a DNA sequence co-segregating with a high pungency trait in the $F_2$ plants; measuring the thickness of the pericarp in ripe fruit produced by the $F_2$ plants; selecting $F_2$ plants lacking the DNA sequence co-segregating with a high pungency and having thick pericarp; measuring the content of vitamin E, pro-vitamin A and vitamin C in ripe fruit produced by the $F_2$ plants lacking the DNA marker and having thick pericarp; and selecting plants with pepper fruit having vitamin E concentration of at least about 5 mg/100 g FW and optionally at least one of pro-vitamin A concentration of at least about 3 mg/100 g FW and vitamin C concentration in the range of from about 200 mg/100 FW to about 500 mg/100 g FW or a combination thereof.

According to one embodiment, the known commercial plant confers at least one trait selected from the group consisting of high germination rate, vigorous growth, herbicide resistance, insect resistance, resistance to at least one bacterial, fungal or viral disease and resistance to various types of non-biotic stress.

According to one embodiment, the DNA sequence co-segregating with a high pungency comprises a polynucleotide sequence as set forth in SEQ ID NO:3 or a fragment thereof.

According to one embodiment of the present invention the steps of crossing and selecting are repeated at least once.

According to another embodiment, the method further comprises the steps of selfing, at least once, the selected plants, and further selecting plants with edible pepper fruit having the vitamin content described above while being non-pungent and having a thick pericarp.

According to yet another embodiment, there are provided pepper plants according to the present invention, wherein the plants or progeny or parts thereof have been transformed so that its genetic material contains one or more transgenes operably linked to one or more regulatory elements. Pepper plants and parts thereof produced from the transformed varieties are also encompassed within the scope of the present invention. According to one embodiment, the transformed gene or genes confer a characteristic selected from the group consisting of herbicide resistance, insect resistance, resistance to a bacterial, fungal or viral disease, male sterility and vigorous growth.

These and further embodiments will be better understood in conjugation with the figures, description and claims below.

DETAILED DESCRIPTION OF THE INVENTION

Figure 1:
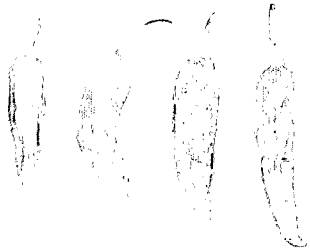
FIG. 1 shows fruit of the pepper plants used as a starting martial and scheme of the selection process.
Figure 1:
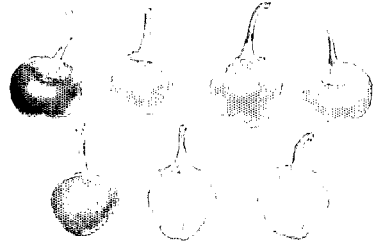
Figure 1:
Figure 1:

The present invention relates to the growing need to supplement the diet of mammals, specifically humans, with vitamins, due to an imbalanced food intake. Obtaining the recommended daily allowance (RDA) of vitamins from natural sources requires consumption of large quantities of fruit and vegetables. However, the dietary intake of most modern population includes only a small portion of fresh fruit and vegetables, and therefore does not provide the recommended intake of essential vitamins.

Thus, it is an object of the present invention to provide fresh edible pepper fruit comprising from about 25% to about 50% of the RDA of vitamin E in a serving of one pepper fruit. It is a further object of the present invention to provide pepper fruit comprising the above-identified vitamin E content, further comprising from about 70% to about 100% of the RDA of pro-vitamin A and/or vitamin C. Preferably, the pepper fruit further comprises an elevated content of total carotenoids.

DEFINITIONS

As used herein, the term "vitamin E" refers to natural D-α-tocopherol. The term "pro-vitamin A" refers to pro-vitamin A carotenoids, specifically carotenoids selected from the group consisting of β-carotene, α-carotene and β-cryptoxanthin, which can be converted to retinol, the most active form of vitamin A in the mammal body. The term Vitamin C refers to ascorbic acid.

As used herein, "edible fruit" and "fresh edible fruit" refer to fruit picked from the plant that are suitable for human consumption without any further processing.

As used herein the term "non-pungent pepper fruit" refers to a fruit having a low level of capsaicin (8-methyl-n-vanillyl-6-nonenamide), dihydrocapsaicin (8-methyl-n-vanillyl-nonanamide), and their precursors. Fruit taste was examined by a panel of independent volunteers. Specifically, "low capsaicin level" refers to less than 0.003% capsaicin, preferably less than 0.001%.

As used herein, the term "trait" refers to characteristic or phenotype. For example, in the context of the present invention "pungency" relates to the taste of a pepper fruit and to its capsaicin level as described hereinabove. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; a recessive trait manifests itself only when present at homozygous state.

The term "pericarp" as is known in the art refers to the wall of a matured ovary. Specifically, pepper fruit pericarp refers to the fruit wall, which is the colored, edible part of the pepper fruit.

As used herein, the term "thick pericarp" refers to a pericarp width of at least 5 mm, preferably at least 8 mm.

As used herein the term "selfing" refers to a controlled self-pollination of a plant, i.e. contacting pollen and ovule produced by the same plant. The term "crossing" refers to controlled cross-pollination, i.e. contacting pollen and ovule each produced by a different plant.

The term "plant vigor" is used herein in its broadest sense, referring to the plant general strength.

As used herein, the term "average" refers to the mean of vitamin E concentration plus or minus standard deviation. The average value is obtained by measuring the vitamin E concentration of a fully ripened fruit crop obtained by stress free cultivation.

As used herein, a "fruit crop" refers to the crop of a single plant, or preferably, to the fruit crop obtained from pepper plants grown on a commercial scale.

The term "commercial pepper strain" as is used herein refers to a pepper strain which is available commercially, having sweet, edible fruit with a thick pericarp. Typically, the commercial pepper strain has fruit with a blocky, Californian-type fruit shape.

According to one aspect, the present invention provides a pepper plant having fruit with altered vitamin content as compared with fruit of currently available commercial pepper strains, the fruit comprising an elevated vitamin E content, further comprising at least one of an elevated pro-vitamin A content, an elevated vitamin C content and combinations thereof, wherein the concentration of vitamin E is at least about 5 mg/100 g FW. According to certain embodiments, the fruit are non-pungent and have a thick pericarp.

According to one embodiment, the fruit comprise at least about 7 mg/100 g FW Vitamin E, preferably at least about 9 mg/100 g FW, more preferably at least about 11 mg/100 g FW vitamin E.

Tocopherols are secondary metabolites synthesized in plastids (mainly chloroplasts) of higher plants. In plastids, tocopherols account for up to 40% of the total quinone pool. Tocopherols are produced by the isoprenoid biosynthesis pathway. The biosynthesis of α-tocopherol (vitamin E) in higher plants involves condensation of homogentisic acid and phytylpyrophosphate to form 2-methyl-6 phytylbenzoquinol that can, by cyclization and subsequent methylations, form various tocopherols. Tocopherols and tocotrienols (unsaturated tocopherol derivatives) are well known antioxidants, and play an important role in protecting cells from free radical damage. Tocopherols not only perform vital functions in plants, but are also important from mammalian nutritional perspectives. Tocopherols, specifically vitamin E, are associated with the prevention of many diseases, including cardiac diseases, cancer, cataracts, retinopathy, neurodegeneration and Alzheimer's disease. Vitamin E has been also shown to have beneficial effects on symptoms of arthritis, and as an anti-aging agent. Vitamin E is also used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products. Natural tocopherols are known to be more biopotent than racemic mixtures of synthetically produced tocopherols. Naturally occurring tocopherols are all D-stereomers, whereas synthetic α-tocopherol is a mixture of eight D,L-α-tocopherol isomers, only one of which (12.5%) is identical to the natural D-α-tocopherol. Natural D-α-tocopherol has the highest vitamin E activity (1.49 IU/mg) when compared to other natural tocopherols or tocotrienols. The synthetic α-tocopherol has a vitamin E activity of 1.1 IU/mg.

Commercially available non-pungent edible pepper fruit comprise low amount of vitamin E. In one embodiment, the pepper fruit of the present invention comprise more than two fold vitamin E concentration compared to its concentration in hitherto known, commercially available sweet pepper fruit, which typically comprises about 1.5-3 mg/100 g FW vitamin E.

The pepper plants of the present invention originate from populations, introductions, cultivars and varieties of pepper, mostly of the species *Capsicum annum* but also of other species, including *C. frutescens, C. chinense, C. baccatum* and *C. chacoense*. During the screening process, plants having fruit with high vitamin E content were identified. However these wild-type plants are not suitable for the production of edible pepper fruit (typically due to pungency and/or thin, hard to chew pericarp). The present invention now provides pepper plants having fruit with an elevated vitamin E content, which are non-pungent, have a thick pericarp and are suitable for marketing as fresh edible produce. Furthermore, the pepper plants of the present invention are suitable for growth on a commercial scale.

According to another embodiment, the present invention provides a pepper plant having fruit comprising at least about 5 mg/100 g FW vitamin E, further comprising at least one of pro-vitamin A and vitamin C.

According to one embodiment, the pro-vitamin A concentration is at least about 3 mg 100/g FW, preferably about 4 mg/100 g FW, more preferably at least about 6 mg/100 g FW.

The pro-vitamin A carotenoids biosynthesis is also part of the larger isoprenoid biosynthesis pathway. Carotenoid hydrocarbons are referred to as carotenes, whereas oxygenated derivatives are referred to as xanthophylls. The carotenoid pathway in plants produces carotenes, such as α-carotene, β-carotene, and lycopene, and xanthophylls, such as lutein. The biosynthesis of carotenoids involves the condensation of two molecules of the $C_{20}$ precursor geranylpyrophosphate to yield the first $C_{40}$ hydrocarbon phytoene. In a series of sequential desaturation reactions, phytoene yields lycopene. Lycopene is the precursor of the cyclic carotenes, β-carotene and α-carotene, which may be converted to vitamin A. Mammals, including human, are capable of converting carotenes to retinol in the liver. Retinol is the most active form of vitamin A, and β-carotene is the best source for retinol as one molecule of β-carotene is cleaved to two molecules of retinol. Commercial red pepper fruit typically comprise about 1 to 1.5 mg β-carotene per 100 gram fresh weight, compared to about two-fold β-carotene concentration of about 2 g/100 g FW in pepper fruit of the present invention.

In general, carotenoids are pigments which give fruit their yellow-orange-red color, and are therefore more abundant in such fruit. The ketocarotenoids, capsanthin and capsorubin occur only in red pepper and contribute to their red color. According to certain embodiments, the pepper fruit of the present invention comprise an elevated content of total carotenoids of at least 70 mg/100 g FW.

According to another embodiment, the vitamin C concentration in the fruit produced by the plants of the present invention is at least about 200 mg/100 g FW. Vitamin C (L-Ascorbic acid) is found in fruit and vegetables. Recently it has been shown that the biosynthesis of L-ascorbic acid in plants occurs through D-galacturonic acid, a principal component of cell wall pectins. GalUR, encoding a D-galacturonic acid reductase, controls vitamin C synthesis and can be used to increase vitamin C production in plants.

In general, pepper fruit are not considered as a good source for vitamin C, since these fruit typically comprise about 100 mg vitamin C per 100 gram fresh weight. An elevated amount of vitamin C according to the present invention refers to pepper fruit comprising at least two fold such concentration, i.e. at least 200 mg/100 g FW. The presence of high concentrations (typically more than about 500-600 mg/100 g FW) of the acidic vitamin C confers sour taste to fruit. The definition of a fruit as a "good" source of vitamin C thus depends not only on the absolute amount of vitamin C per 100 gram fresh weight, but also on the palatability of the fruit. A very sour fruit, which may be consumed only at a very small serving size, would not provide the required daily allowance. According to one preferred embodiment, the plants of the present invention provides fruit comprising vitamin C concentration in the range of 200-500 mg/100 g FW.

According to another aspect, the present invention provides pepper plants that yield fruit crops with altered vitamin content comprising an elevated vitamin E content, further comprising at least one of an elevated pro-vitamin A content, an elevated vitamin C content and combinations thereof as compared with vitamin levels found in edible pepper fruit of currently available commercial strains, wherein the average crop concentration of vitamin E is at least 5 mg/100 g FW. According to certain embodiments, the fruit are non-pungent and have a thick pericarp.

The content of vitamin E, pro vitamin A (β-carotene) and vitamin C in the pepper fruit produced by the plants of the present invention is measured using techniques as are known to a person skilled in the art. Typically the concentration of vitamin E, β-carotene, the pro-vitamin A, and total carotenoids is measured by High Performance Liquid Chromatography (HPLC). Measurements of ascorbic acid concentration are based on colorimetric reactions as described in the Examples section hereinbelow. However, it is to be understood that while these methods were used to demonstrate the vitamin content of the fruit of the present invention, any other method by which the content of vitamin E, pro-vitamin A, vitamin C and total carotenoids can be measured is also encompassed within the scope of the present invention.

The vitamin profile of the pepper fruit according to the present invention can represent the content of each vitamin in a single fruit as well as the average fruit crop content of each vitamin. The fruit crop can refer to fruit produced by a single plant, or, preferably, to the fruit crop produced by plants grown on a commercial scale. As used herein, the term "average crop content" refers, for example, to the mean plus or minus standard deviation of the vitamin E concentration measured for a ripe pepper crop obtained by stress free cultivation.

The content of vitamins, specifically the content of vitamin E in the pepper fruit of the present invention is influenced by the growth conditions of the pepper plants, the ripening stage and the storage conditions of the pepper fruit. As exemplified hereinbelow, high growth temperature (day/night temperature of 29° C./21° C. respectively) resulted in two-fold vitamin concentration compared to low growth temperatures (day/night temperature of 20° C./12° C. respectively). Vitamin content in fully ripen fruit is stable during storage, while vitamin E concentration in fruit picked before complete ripening may increase with time.

Therefore, throughout the present invention, the values indicated for vitamin concentration in the fruit of the present invention represents values measured in full ripen fruit freshly picked from plant grown under stress free environmental conditions.

The pepper plants of the present invention can be genetically stable inbred lines as well as hybrids produced by crossing two different strains. As used herein, parent lines refers to open pollinated, inbred lines, stable for the desired traits over cycles of self-pollination and planting.

The parent lines of the present invention were developed from a cross between breeding strains selected for their high vitamin content and commercially available, vigorous pepper plants selected from a germplasm collection of proprietary breeding material belonging to one of the applicants of the present invention.

The development of a commercial, superior pepper strain requires a significant breeding effort. High variation is found within different pepper populations and therefore they can serve as a source for new or desired traits. However, a plant having a desired trait is not necessarily useful for commercial scale production, as it may have undesirable traits such as poor germination rate, low vigor, low fruit yield, small fruit, susceptibility to diseases, etc. Specifically, high vitamin content is typically linked to pungency and/or thin pericarp, and the breeding program of the present invention aimed at breaking this linkage, using a molecular DNA marker for pungency. Pungency in *Capsicum* fruit is due to the accumulation of the alkaloid capsaicin and its analogs. The biosynthesis of capsaicin is restricted to the genus *Capsicum* and results from the acylation of an aromatic moiety, vanillylamine, by a branched-chain fatty acid. Pungency was reported to be linked to the Pun1 locus. Recently, it has been found that Pun1 encodes an acyltransferase critical to capsaicinoid biosynthesis, present in pungent pepper fruit (e.g. Pun1 gene from *Capsicum annuum* cultivar That Hot, Accession No. AY819029; SEQ ID NO:4; Stewart C et al., Plant J. 42(5): 675-88 2005). The recessive allele, pun1, which was known to be associated with lack of pungency, results from a large deletion at this locus (Accession No. AY819031, partial sequence; SEQ ID NO:5). The deletion was found to be of 2.5 kb, spanning 1.8 kb of the putative promoter and 0.7 kb of the first exon. (Stewart C et al., supra). Accordingly, sequences from within this deletion can serve as markers for pungency, wherein plants having a genome lacking such sequences produced non-pungent fruit. The DNA marker used according to certain currently preferred embodiments of the present invention is a fragment of about 700 bp from within the promoter region of the Pun1 gene (positions 666 to 1397 of SEQ ID NO:4, designated herein as SEQ ID NO:3). Thus, plants lacking this DNA fragment, having a polynucleotide sequence as set forth in SEQ ID NO:3, are homozygous for the recessive pun1/pun1 gene, and are therefore non-pungent.

In addition, the pepper plants of the present invention produce fruit having a combination of vitamins at high concentration, wherein such combination is not present in hitherto known pepper fruit.

As used herein, the term "germination rate" refers to the percentage of seedling emerging from sowed seeds. "Poor germination rate" refers to seedling emergence of less 80% out of the sowed seeds, and poor uniformity of emerging seedlings. The term "non biotic stress" as used herein, refers to environmental conditions unfavorable for plant growth, including, but not limited to, low temperature, limited supply of water, soil salinity, sub-optimal light intensity and any combination thereof. "Low temperature" with regard to pepper plant growth according to the present invention refers to temperature below 10° C.

The breeding program of the present invention started with the screening of several hundred plants from populations, introductions, cultivars and varieties of pepper, mostly from the species Capsicum annum and few from other species including C. frutescens, C. chinense, C. baccatum and C. chacoense. The plants were analyzed for the carotenoid spectrum, β-carotene (pro-vitamin A) concentration and total content of vitamin C and E.

Plants having fruit showing the highest content of one or more of vitamin E, pro-vitamin A (β-carotene) and vitamin C were selected. Each of these plants was transferred from the field to the greenhouse for controlled selfing. The fruit produced by the plants were examined for their vitamin content, and three strains were selected: one having fruit with high vitamin E content ("HE"); one having fruit with high pro-vitamin A (β-carotene) content ("HPA") and one with high vitamin C content ("HC").

A cross was made between HA and HC, and between HE and a commercial strain having desirable agricultural traits to obtain $F_1$ plants. The two $F_1$ populations were then crossed to produce $F_2$ plants. The $F_2$ plants were screened for horticultural traits including plant vigor; time and uniformity of fruit-set; yield; fruit size, shape; pericarp thickness; texture; color; presence of fractures on the fruit skin and scored according to their fruit quality. In addition, the plants were screened for the presence of the DNA marker for pungency. Plants having fruit with high score and devoid of the DNA marker for pungency were selected for vitamin content analysis. Plants having fruit showing also a high content of at least one of vitamin E, pro-vitamin A and vitamin C were selected for further breeding. These plants were first selfed to obtain $F_3$ population. $F_3$ plants that preserved their ability to produce high-scored fruit (i.e. fruit showing the desirable horticulture traits and high vitamin content) were taken for further breeding (FIG. 1). Crosses were made between selected plants and between selected plants and commercial strains having desirable horticultural traits. Stability of the traits was verified by examining plants grown from seeds obtained by self-pollination.

According to one embodiment, the present invention provides a method for producing pepper plants having edible fruit with altered vitamin content as compared with edible fruit of currently available commercial pepper strains, while being non-pungent and having a thick pericarp, comprising the steps of: selecting at least one pepper plant having fruit comprising an elevated vitamin E content, at least one pepper plant having fruit comprising an elevated pro-vitamin A content and at least one pepper plant having fruit comprising an elevated vitamin C content as compared with the edible fruit of currently available commercial pepper strains; crossing the at least one pepper plant having fruit comprising an elevated vitamin E content with a known commercial plant to produced a first $F_1$ population; crossing the at least one pepper plant having fruit comprising an elevated pro-vitamin A content with the at least one pepper plant having fruit comprising an elevated vitamin C content to produced a second $F_1$ population; collecting the seeds of the first and the second $F_1$ populations; growing plants from said first and said second $F_1$ seed populations; crossing at least one plant from said first $F_1$ population with at least one plant from said second $F_1$ population to produce $F_2$ population; collecting the hybrid $F_2$ seeds; growing $F_2$ plants from the $F_2$ seeds; examining the presence of a DNA sequence co-segregating with a high pungency trait in the $F_2$ plants; measuring the thickness of the pericarp in ripe fruit produced by the $F_2$ plants; selecting $F_2$ plants lacking the DNA marker and having a thick pericarp; measuring the content of vitamin E, pro-vitamin A and vitamin C in ripe fruit produced by the $F_2$ plants lacking the lacking the DNA sequence co-segregating with a high pungency and having a thick pericarp; and selecting plants with pepper fruit having vitamin E concentration of at least about 5 mg/100 g FW and at least one of pro-vitamin A concentration of at least about 3 mg/100 g FW; vitamin C concentration in the range of from about 200 mg/100 FW to about 500 mg/100 g FW; or any combination thereof.

According to one embodiment, the known commercial plants confer at least one characteristics selected from the group consisting of high germination rate, vigorous growth, herbicide resistance, insect resistance, resistance to a bacterial, fungal or viral disease and resistance to various types of non-biotic stress. Particularly, the known commercial plant was selected so as to confer resistance to pepper mild mottle virus (PMMV) race 3 and/or tomato spotted wilt tospovirus (TSWV), thick pericarp, and desirable fruit size and shape.

According to one embodiment, the DNA sequence co-segregating with a high pungency comprises a polynucleotide sequence as set forth in SEQ ID NO:3 or a fragment thereof.

According to one embodiment of the present invention the steps of crossing and selecting are repeated at least once.

According to another embodiment, the method further comprises the steps of selfing, at least once, the selected plants, and further selecting plants with pepper fruit having vitamin E concentration of at least about 5 mg/100 g FW; pro-vitamin A concentration of at least about 3 mg/100 g FW; vitamin C concentration in the range of from about 200 mg/100 FW to about 500 mg/100 g FW; or combinations thereof, the fruit being non-pungent and having thick pericarp.

According to one embodiment, the plants produced by the methods of the present invention are genetically stable inbred lines. According to another embodiment, the plants are hybrids produced by crossing two inbred lines.

According to another aspect, the present invention provides a method for producing first generation ($F_1$) hybrid pepper seeds.

According to one embodiment, the present invention provides a method for producing first generation hybrid seeds comprising crossing a first stable inbred pepper plant with a second stable inbred pepper plant and harvesting the resultant hybrid $F_1$ seeds, wherein the first and the second stabilized inbred plants are pepper plants having fruit selected for having altered vitamin content compared with the edible fruit of currently available commercial strains, specifically comprising an elevated vitamin E content, and further comprising at least one of an elevated pro-vitamin A content, an elevated vitamin C content or a combination thereof, while being non-pungent and having a thick pericarp.

According to another embodiment, the present invention also provides a first generation $F_1$ hybrid pepper plants that are produced by growing the hybrid pepper seeds produced by the above-described method. The $F_1$ plants not only have fruit with high vitamin content, but they are also suitable for agricultural use, having horticultural traits which are comparable to known, commercially available hybrids.

Hybrid ACE05F01-521 seeds of which were deposited with NCIMB Ltd. Ferguson Building, Craibstone Estate, Bucksburn, Aberdeen, AB21 9YA Scotland, UK on Mar. 9, 2006 under accession No. 41381, serve as an example to a hybrid plant having fruit with altered vitamin content. Specifically, the fruit of plants grown from these seeds comprise about 9 mg/100 g FW vitamin E, about 5 mg/100 g FW pro-vitamin A ([beta]-carotene) and about 260 mg/100 g FW vitamin C. *Capsicum annuum* strains 8701, 8703, and 8704 serve as further examples for the plants of the present invention. Seeds of *Capsicum annuum* 8701, 8703 and 8704 were deposited with NCIMB Ltd. Ferguson Building, Craibstone Estate, Bucksburn, Aberdeen, AB21 9YA Scotland, UK, on Jul. 2, 2009 under Accession Numbers 41641, 41642 and 41643, respectively. These strains serve as further examples to a hybrid plant having non-pungent fruit with elevated vitamin content. Specifically, the fruit of plants grown from these seeds comprise between 5.3 to 5.8 mg/100 g FW vitamin E, between 3.4 to 4.7 mg/100 g FW pro-vitamin A ([beta]-carotene) and between 250 to 280 mg/100 g FW vitamin C.

The present invention also relates to seeds harvested from the $F_1$ hybrid pepper plants and to plants grown from these seeds. A common practice in plant breeding is using the method of backcrossing to develop new varieties by single trait conversion. The term single trait conversion as used herein refers to the incorporation of new single gene or allele into a parent line wherein essentially all of the desired morphological and physiological characteristics of the parent lines are recovered in addition to the single gene or allele transferred. The term backcrossing as used herein refers to the repeated crossing of a hybrid progeny back to one of the parental pepper plants. The parental pepper plant which contributes the gene or allele for the desired characteristic is termed the nonrecurrent or donor parent. This terminology refers to the fact that the nonrecurrent parent is used one time in the backcross protocol and therefore does not recur. The parental pepper plant to which the gene(s) or allele(s) from the nonrecurrent parent are transferred is known as the recurrent parent as it is used for several rounds in the backcrossing protocol. In a typical backcross protocol, a plant from the original varieties of interest (recurrent parent) is crossed to a plant selected from second varieties (nonrecurrent parent) that carries the single gene/allele of interest to be transferred. The resulting progeny from this cross are then crossed again to the recurrent parent and the process is repeated until a pepper plant is obtained wherein essentially all of the desired morphological and physiological characteristics of the recurrent parent are recovered in the converted plant, in addition to the single transferred gene or allele from the nonrecurrent parent. Backcrossing methods can be used with the present invention to improve or introduce a characteristic into the parent lines.

The present invention encompasses any part of the stabilized parent plant or of the hybrid plant, including pollen, ovules and tissue cultures regenerated from these plants. Pollen and ovules are used in breeding programs, in general and as described by the present invention. Tissue culture of pepper can be used for the in vitro regeneration of a pepper plant as is well known in the art.

Plants comprising within their pedigree a pepper plant having fruit with altered vitamin content according to the present invention, and methods for producing same, are also encompassed within the scope of the present invention.

The present invention further provides seeds of pepper wherein the plants grown from the seeds have edible fruit with altered vitamin content comprising an elevated vitamin E content, further comprising at least one of an elevated pro-vitamin A content, an elevated vitamin C content and combinations thereof, wherein the concentration of vitamin E is at least about 5 mg/100 g FW. According to certain embodiments, the fruit are non-pungent and have a thick pericarp.

According to one embodiment, the plants grown from the seeds have fruit comprising at least about 7 mg/100 g FW vitamin E, preferably at least about 9 mg/100 g FW, more preferably at least about 11 mg/100 g FW.

According to another embodiment, the plants grown from the seeds have fruit comprising at least 5 mg/100 g FW vitamin E, further comprising pro-vitamin A. According to yet another embodiment, the plants grown from the seeds have fruit comprising at least 5 mg/100 g FW vitamin E, further comprising vitamin C. According to yet another embodiment, the plants grown from the seeds produce fruit comprising at least 5 mg/100 g FW vitamin E, further comprising pro-vitamin A and vitamin C.

According to one embodiment, the pro-vitamin A concentration in the fruit produced by the plants grown from the seeds is at least about 3 mg/100 g FW, preferably about 4 mg/100 g FW, more preferably about 6 mg/100 g FW, and the vitamin C concentration is at least about 200 mg/100 g FW, preferably in the range of from about 200 mg/100 FW to about 500 mg/g FW.

According to still further embodiment, pepper fruit produced by the plants grown from the seeds comprise at least about 5 mg/100 g FW vitamin E, further comprise at least about 3 mg/100 g FW pro-vitamin A, at least about 200 mg/100 g FW vitamin C and an elevated content of total carotenoids. According to one embodiment, the total carotenoids concentration is at least about 70 mg/100 g FW.

According to yet another embodiment, the present invention provides robust pepper plants according to the present invention, wherein the plants or progeny or parts thereof have been transformed so that their genetic material contain one or more transgenes operably linked to one or more regulatory elements. Pepper plants and parts thereof produced from the transformed plants are also encompassed within the scope of the present invention. According to on embodiment, the transformed gene or genes confer a characteristic selected from the group consisting of herbicide resistance, insect resistance, resistance to bacterial, fungal or viral disease, male sterility and vigorous growth.

According to another aspect, the present invention provides edible pepper fruit having altered vitamin content compared with the edible fruit of currently available sweet edible fruit, specifically an elevated vitamin E content, preferably further comprising an elevated pro-vitamin A content and an elevated vitamin C content. The fruit can be marketed as a fresh product or the fresh fruit can serve as a source for processed, high-vitamin pepper products. Pepper and pepper product consumption is growing constantly due to the development of new varieties which permit supply all year long, and to the increased awareness to the general nutritional benefit of fruit.

According to one embodiment, the edible pepper fruit comprises at least about 5 mg/100 g FW Vitamin E, preferably at least about 7 mg/100 g FW, more preferably at least about 9 mg/100 g FW most preferably at least about 11 mg/100 g FW vitamin E.

According to another embodiment, the present invention provides edible pepper fruit comprising at least about 5 mg/100 g FW vitamin E, further comprising an elevated content of pro-vitamin A. According to yet another embodiment, the edible pepper fruit comprising at least about 5 mg/100 g FW vitamin E, further comprises an elevated content of vitamin C. According to a further embodiment, the edible pepper fruit comprising at least about 5 mg/100 g FW vitamin E further comprises an elevated content of pro-vitamin A and vitamin C. According to certain embodiments, the fruit are non-pungent and have a thick pericarp.

According to one embodiment, the pro-vitamin A concentration in the fruit is at least about 3 mg/100 g FW, preferably about 4 mg/100 g FW more preferably 6 mg/g FW. According to another embodiment, the vitamin C concentration in the fruit is at least about 200 mg/g FW, preferably in the range of from about 200 mg/100 FW to about 500 mg/100 g FW.

According to still further embodiment, the present invention provides edible pepper fruit comprising at least about 5 mg/100 g FW vitamin E, further comprising at least about 3 mg/100 g FW pro-vitamin A, at least 200 mg/100 g FW vitamin C and an elevated content of total carotenoids. According to one embodiment, the total carotenoids concentration is at least about 70 mg/100 g FW.

It should be understood that although the invention is described specifically in reference to pepper plants having edible fruit with an elevated content of vitamins, specifically vitamin E concentration of at least about 5 mg/100 g FW, pro-vitamin A concentration of at least about 3 mg/100 g FW and vitamin C concentration in the range of from about 200 mg/100 FW to about 500 mg/g FW, other plant species having fruit with such elevated vitamin content are also contemplated within the scope of the present invention. The selection methods of the present invention can be used to produce a wide variety of plant species having fruit with an elevated content of vitamin E, pro-vitamin A and/or vitamin C, as described herein. Thus, any plant species amenable to selection as is known to a person skilled in the art, particularly selection using DNA marker(s), is encompassed within the broad scope of this invention. Such plant species can be of the pepper Solanaceae family, for example tomato and eggplant or plants having edible fruit from other families such as cucumber, pumpkin, and the like.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

EXAMPLES

Example 1

Selection of Pepper Plant Having Elevated Vitamin Concentrations

Several hundred plants from populations, introductions, cultivars and varieties of pepper, mostly from the species *Capsicum annum* and also from other species including *C. frutescens, C. chinense, C. baccatum* and *C. chacoense* were screened. The plants were analyzed for a spectrum of carotenoids including, specifically, β-carotene, and for the concentration of vitamin C and vitamin E. Three breeding strains were developed through controlled selfing of several generations of plants having fruit rich in at least one of vitamin E, carotenoids and vitamin C, as follows:

A) Strain E-8511, a paprika type pepper originating from a segregating population of a breeding program aimed at the development of relatively high stability of the red color of paprika. Its vitamin E content was the highest among all the populations analyzed, about 12.5 mg/100 g fresh weight of the fruit pericarp. The fruit had a thin pericarp and its taste was very pungent.

B) Strain CLR-7174, a strain having fruit with a very intense color and carotenoid content of about 185 mg/100 g FW, of which about one tenth is β-carotene. The strain was specifically developed for high carotenoid content, and was a paprika type pepper producing fruit with thin pericarp.

These two selected strains produce fruit which are suitable for the production of ground powder, but not for use as a fresh edible produce, as the fruit pericarp tends to dry before the fruit is ready for picking.

C) Strain C-8271, having a very high content of vitamin C of more than 750 mg/100 g fruit FW. This strain originated from an introduction of ornamental pepper obtained from The Israel Gene Bank and is a cherry pepper type, with a rounded, small and highly pungent fruit.

These three strains, together with a fourth commercial "Maor" cultivar, having blocky, California-type fruit, were used as parents in a four parents' cross for the development of breeding strains combining high content of one or more of the vitamins E, C, and pro-vitamin A with desired agronomical characters of the plant and the fruit.

The four parents' cross was performed as shown below and in FIG. 1:

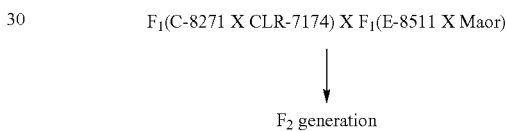

More than ten thousands plants of the $F_2$ generation were grown in the field and screened for agronomical traits, including: fruit size, shape and color; time and uniformity of fruit set; growth habitat; and susceptibility to diseases—including pathogen types and occurrence frequency. To select fruit which are non-pungent, the presence of a DNA marker for pungency was examined, as described in Example 2 hereinbelow.

Thirty-one $F_2$ plants combining two or more desirable traits were selected from the $F_2$ generation of the four parents' cross. These plants were advanced to $F_6$ generation through controlled selfing and progeny tests.

These breeding strains were grown under different climate conditions. The best performing strains were crossed with breeding lines from the germplasm of Hazera Genetics Ltd. harboring genes for resistance to various widespread diseases of peppers.

Example 2

Selection of Plants Having Non-Pungent Fruit Using Molecular DNA Marker

The presence or absence of pungency is controlled by a single dominant gene Pun1 (Stewart C et al., supra). Plants that are homozygous recessive to this gene (pun1/pun1) do not develop pungency in the fruit. The recessive gene has a 2.5 kb deletion compared to the dominant gene, that spans from the promoter to the first exon of the gene. The marker used is a product of about 700 bp of a PCR reaction, using the following primers:

Forward (PT-1): 5'-GACCACGGGTCTACGGATAGACCTC-3' (SEQ ID NO:1)

Backward (PT-2): 5'-CAAACCTCGCCTTCGTGACAATCCCA-3'. (SEQ ID NO:2)

Figure 2:
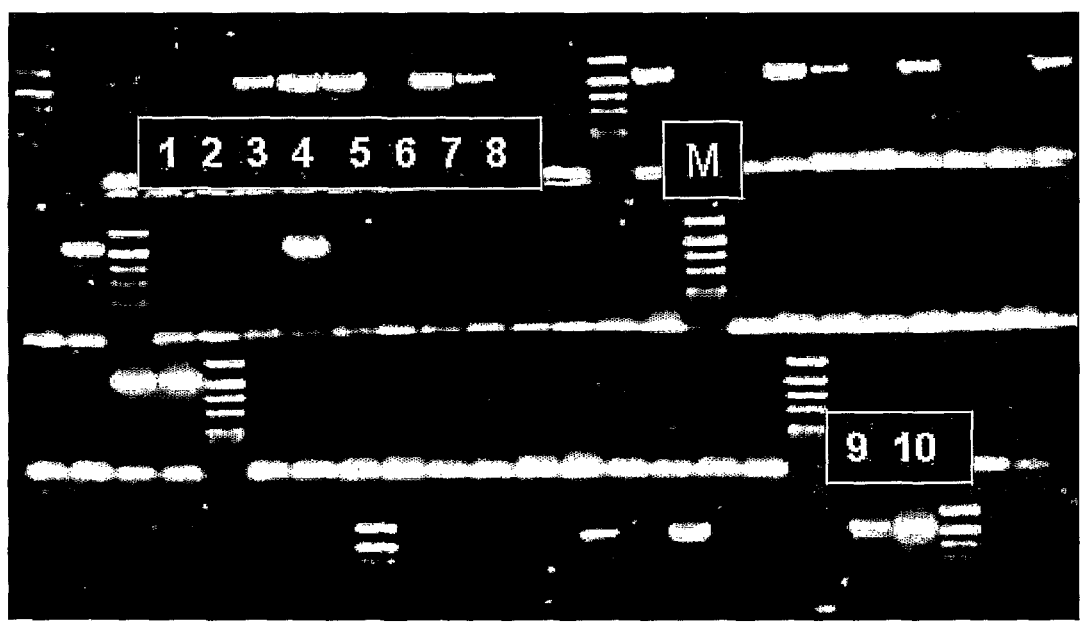
FIG. 2 shows a typical picture of an agarose gel loaded with PCR products. The presence of a band of about 700 bp indicates samples obtained from plants having pungent fruit (for example, lanes 4; 9-10). Absence of this band indicates non-pungent fruit (for example, lanes 1-3; 5-8). Lane M indicates size marker-pBR322/AluI.

The resulted DNA fragment of about 700 bp is located within the promoter of the Pun1 gene, and thus only plants having pungent pepper fruit will show the expected 700 bp fragment (FIG. 2).

DNA was isolated from examined plants by a standard method, as is known in the art, and subjected to a PCR reaction using the above-identified primers under the following conditions:

PCR Reaction Mixture:

| | |
|---|---|
| Buffer × 10 (without MgCl$_2$) | 2.5 µl |
| MgCl$_2$ (2.5 mM) | 1.5 µl |
| dNTPs (10 mM) | 4 µl |
| Primers (PT-1 + PT-2) 100 ng/µl | 2 µl + 2 µl |
| Taq Polymerase | 0.2 µl (1U) |
| H$_2$O | 10.8 µl |
| DNA | 2 µl (of 100 ng/µl) |
| Total volume | 25 µl |

PCR Program:

| Stage | Temperature | Time (In PCR PC-100 MJ Research Inc.) |
|---|---|---|
| 1 | 94° C. | 1 min |
| 2 | 94° C. | 1 min |
| 3 | 68° C. | 1 min |
| 4 | 72° C. | 10 min |
| 5 | | 39 cycles of stages 2-4 |
| 6 | 72° C. | 10 min |
| 7 | 6° C. | Not limited |

After the completion of the PCR program, the samples were loaded onto a 1.5% agarose gel and run at 80-120V until a clear band appears for control samples.

The PCR method enables the simultaneous examination of a multiplicity of DNA samples. FIG. 1 shows a typical picture of an agarose gel, loaded with a marker, and DNA isolated from plants known to have pungent fruit (positive control) and from examined plants. Absence of the 700 bp band indicates that the DNA samples were isolated from plants having non-pungent fruit.

Example 3

Measurement of Vitamin Concentrations

Determination of Carotenoid Content in Pepper Fruit

Saponification: Red pepper fruit to be examined were freeze-dried and the dry material was grounded to a powder using a coffee machine. 30 mg of the freeze-dried powder were introduced into 7.5 ml ethanol solution containing 2% BHT and 1.25 ml KOH 60%. The mixture was incubated at 37° C. for 30 minutes with the introduction of N$_2$ gas into the solution.

Extraction: 5 ml H$_2$O was added to the saponified mixture, and the mixture was incubated for 10 min. in room temperature. 5-ml hexane were then added, the mixture was stirred, and than left until the hexane and the water fractions separated.

The hexane fraction containing the extracted carotenoids was then collected. The extraction procedure was repeated 5 times until no more color (i.e., no visible amount of carotenoids) was detected. The residual H$_2$O in the hexane fraction was dried with sodium sulfate. The hexane was evaporated to dryness with N$_2$ gas and the carotenoids were solubilized by 1 ml of acetone. The sample was filtered through a 0.2µ filter and injected into the HPLC system.

Measurement of carotenoid concentration by HPLC: measurements were performed using Shimadzu LC-10A HPLC. The system contains an auto-injector and detector diode array (SPD-M10AVP). The column Lichrosphare-100, RP-18.5, 250 mm×5 µm particles was used for carotenoid separation. A guard column (Lichrosphare-4-4 RP-18.5 µm) was also used. The carotenoids were eluted with a mixture of solution A: acetone and B: H$_2$O, at a flow rate of 1 ml/min, using a gradient of the H$_2$O (25%-0, in 37 min). The best separation was obtained with the following empirical gradient:

| Time (min): | 0 | 15 | 12 | 5 | 5 |
|---|---|---|---|---|---|
| % H$_2$O: | 25 | 25 | 5 | 0 | 25 |

The peaks were detected at 474 nm and 460 nm.

Total carotenoids were estimated from 100 mg red pepper powder extracted with 25 ml of acetone. The color was determined at 474 nm and calculated for total carotenoids by an extinction coefficient of capsanthin 1%=1905, (Dawson et al., 1969. Data for Biochemical Research, Clarendon Press, Oxford, England p. 328). For peak identification, the Rf-values and absorption spectra were compared with those of standard material as described by Levy et al. (J. of Agric. and Food Chem. 43:362-366, 1995).

Determination of Vitamin E in Pepper Fruit

Red pepper fruit were freeze-dried and the dry material was grounded to a powder using a coffee machine. α-tocopherol from thirty mg of pepper powder was extracted with 3 ml ethanol overnight at 4° C. The ethanol extract was centrifuged at 20,800 g for 3 min. The supernatant was filtered through a 0.2 µm membrane. A 20-µl sample was injected into HPLC (Merck-Hitachi L-6200A) and separated with a Merck Lichrocart column RP-18, 125-4 mm, eluted by an isocratic mobile phase of methanol at a flow rate of 1 ml/min, and detected with a HPLC spectrofluorometer detector (Jasco FP-210). The element was excited at 290 nm and emitted at 329 nm. The results are the averages for three determinations for each sample. D-α-Tocopherol (Sigma) was used for calibration of a standard curve.

Determination of Vitamin C in Pepper Fruit

Fresh pepper fruits were cut to 2×2 cm$^2$ cubes. 5 g fruit cubes were blended with 20 ml of 4% metaphosphoric acid using Waring blender. The resulting juice was centrifuged for 30 min at 23,500 g. Ascorbic acid concentration in the supernatant was measured by reflectometer, using Merck RQflex Kit according to the manufacturer directions. In principle, the assay is based on the reduction of the yellow-colored substance molydophosphoric acid to phosphomolyddenum having a blue color. The values as displayed by the reflectometer are mg ascorbic acid/l, which were converted to mg ascorbic acid/100 g FW.

Vitamin C determination by HPLC: In part of the samples, ascorbic acid concentration was determined by HPLC. The fruit extract taken for the measurements was as described hereinabove. The determination of ascorbic acid by HPLC was carried out with Shimadzu LC-10A HPLC which contains an autoinjector and a diode array detector (SPD-M10Avp). The extracted solution was filtered through a filter of 0.2µ and injected into a column of Merck RP-18e 4×250 mm, 5 µm particles and eluted with an isocratic mobile phase of $KH_2PO_4$ 10 mM/MeOH (97:3 v/v) and tetra butyl ammonium hydroxide 0.75 mM, at a flow rate of 1 ml/min. Ascorbic acid was detected at 268 nm. Ascorbic acid (Merck) was used for calibration of a standard curve Example 4

Vitamin Content and Environmental Factors

During the course of breeding of plants having fruit with altered vitamin content according to the present invention, plants were grown under different environmental conditions so as to identify factors which may influence the vitamin concentration in the fruit.

Experiment 1

Figure 3:
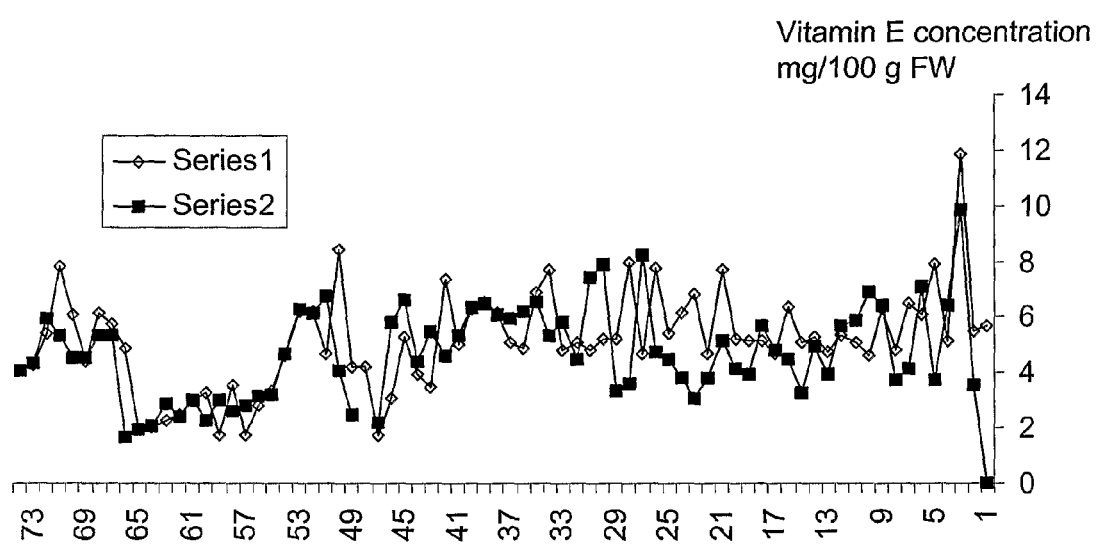
FIG. 3 shows the content of vitamin E (mg/100 g FW) in fruit picked at two time points: November 2002 (series 1) and January 2003 (series 2).

Seventy-four $R_1$-cross plants (primary hybrid plants derived from two parental strains) were planted at the same location, and fruit were collected in November 2002 and January 2003. Therefore, the fruit matured on the plants were exposed to different temperature and light regimes according to the time in the year (warmer with longer days in November compared to January). As is shown in FIG. 3, the vitamin E content was found to depend on the season in which the fruit was picked.

Experiment 2

Figure 4:
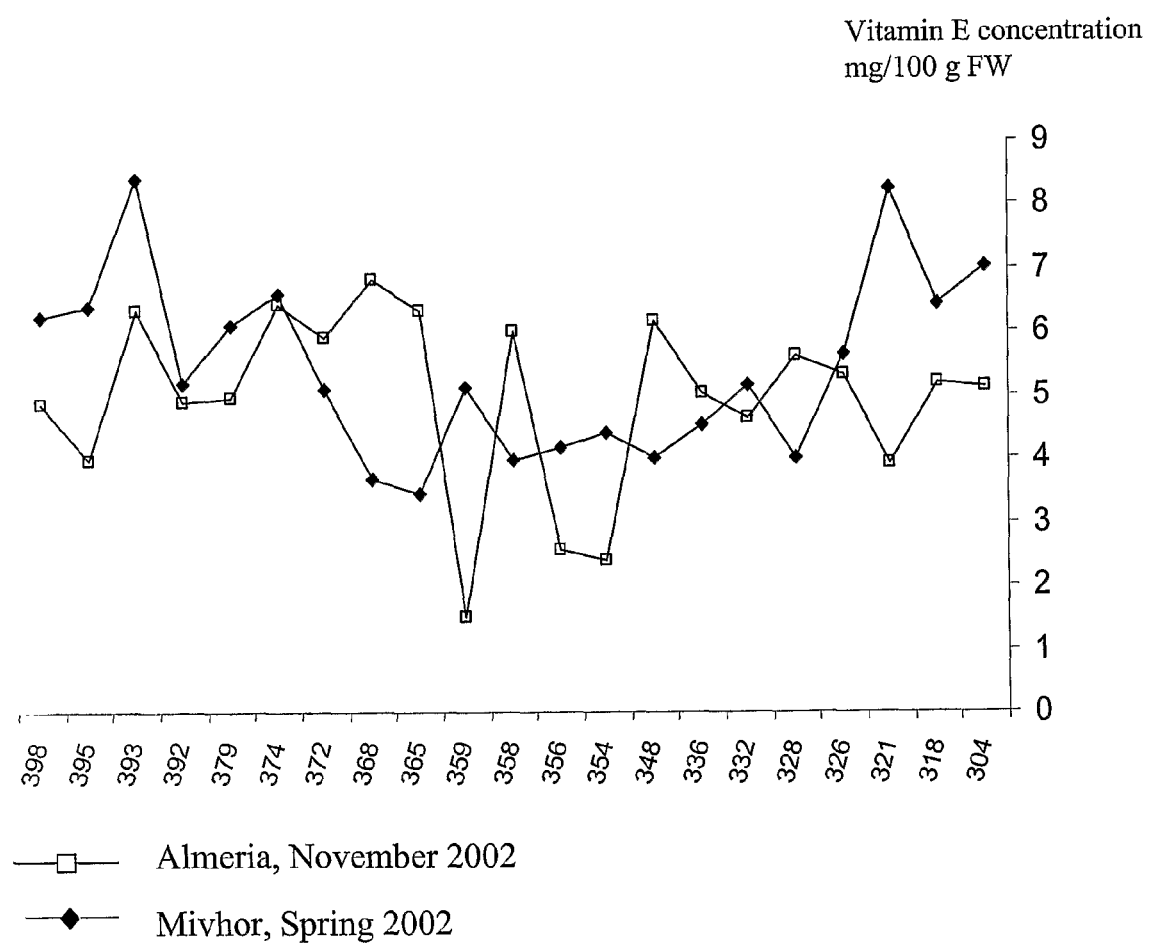
FIG. 4 shows the content of Vitamin E (mg/100 g FW) in fruit picked in November 2002 from plants grown in Almeria, Spain, and in fruit picked in Spring 2002 from plants grown in Mivhor, Israel.

Twenty-one $R_1$-cross plants were planted in two different locations: Mivhor (south Israel) and Almeria (South Spain). Fruit were picked in May 2002 and November 2002, respectively. Fruit from both groups were also picked in November 2002. In these fruit, vitamin E content as well as vitamin C content was measured. As shown in FIG. 4, a significant variation in vitamin E content was observed with regards to the planting location (i.e., different environmental conditions of temperatures, light and irrigation). In both locations, comparable vitamin C concentrations were measured (data not shown).

Experiment 3

Plants were grown under controlled temperature regimes: High temperature (29° C. during the day and 21° C. during the night), and low temperature (20° C. during the day and 12° C. during the night). In addition, plants grown in each temperature regime were divided to three groups. One group obtained full natural light (2000 micro Einstein, µE); one group was grown under 30% shade (1200-1400 µE) and one group was grown under 50% shade (900-1000 µE). Vitamin content (E, pro-A and C) was found not be depended on light intensity. Temperature regime only slightly affected the level of vitamin C and pro-vitamin A. However, high temperature regime increased the vitamin E concentration about two fold.

Experiment 4

Vitamin E and vitamin C concentration was measured in unripe fruit (green fruit) and in fully ripe fruit (red fruit) at picking. In addition, in each group the vitamin concentration was also measured during a storage period of 30 days at 7° C. During storage, vitamin concentration was measured at five time points. The results (mean of 3 replicates) are summarized in Table 1 below.

TABLE 1

Effect of fruit ripening on the concentration of vitamin E and C

| Ripening stage | Time of measurement | Vitamin (mg/100 g FW) | |
|---|---|---|---|
| | | E | C |
| Green fruit | At picking | Low (1.5) | High (270) |
| | During storage | Non-Stable (Increased up to 3.2) | Stable |
| Red fruit | At picking | High (6.6) | High (280) |
| | During storage | Stable | Stable |

As shown in Table 1, high and stable concentrations of Vitamin E and vitamin C are obtained when fruit was picked at ripening.

In summary, the values of vitamin concentrations described throughout the present specification and claims that follow refer to values obtained from ripe fruit from plants grown under favorable conditions, particularly at a temperature above 10° C.

Example 5

Vitamin Content in Fruit Selected During the Breeding Program

The content of vitamin C, vitamin E, pro-vitamin A (β carotene) and total carotenoids was determined in more than one hundred samples. The range of vitamins found in this variable population was (mg/100 g FW) were: vitamin C: 200-600 mg, vitamin E: 2-12 mg, and β-carotene: 1-7 mg. Four parent plant, including one commercial strain and three plants having elevated vitamin content as described in Example 1 hereinabove were selected. Table 2A shows the vitamin concentration in the four parent's strains. Table 2B describes the vitamin concentration of the $F_1$ populations described above.

About 5,000 plantlets grown from seeds of the above-described F1 population were grown in the field ($F_2$ plant population). These $F_2$ plants were screened for horticultural traits including fruit size and shape; presence of fractures on the fruit skin; fruit texture and color; plant vigor; and pericarp thickness. About 300 plants produced fruit having desirable characteristics, and their fruit were further analyzed for vitamin content. Plants having fruit with elevated content of at least one of vitamin E, pro-vitamin A and vitamin C were used further breeding. These plants were self pollinated, and $F_3$ seeds were subjected to further selection for high vitamin content and absence of pungency, which was detected with the DNA marker. This selection process was repeated to obtain stable parent line, having fruit with high vitamin content according to the teaching of the invention, thick pericarp, and being devoid of pungency.

Table 2C shows the vitamin content of pepper fruit obtained from hybrid strain ACE05F01-521, seeds of which were deposited with NCIMB Ltd. Ferguson Building, Craibstone Estate, Bucksburn, Aberdeen, AB21 9YA Scotland, UK on Mar. 9, 2006 under accession number 41381. This hybrid is F1 of ACE05F08-71 as the male parent and ACE05F01-118 as the female parent obtained using successive steps of self-pollination and selection as described above. The vitamin values shown in table 1C are means of representative fruit picked in November 2005 and in January 2006. Strain ACE05F01-521 is described herein as an example of plants producing fruit with elevated vitamin content according to the present invention, and is not meant to be limiting but is illustrative of various pepper types and lines that can be encompassed within the scope of the present invention.

Additional examples of pepper plants having non pungent fruit with elevated content of at least one of vitamin E, pro-vitamin A and vitamin C strains according to the teachings of the present invention are 8701, 8703, and 8704, seeds of which were deposited with NCIMB Ltd. Ferguson Building, Craibstone Estate, Bucksburn, Aberdeen, AB21 9YA Scotland, UK, on Jul. 2, 2009 under Accession Numbers 41641, 41642 and 41643, respectively, as described in Table 3:

TABLE 3 vitamin content of fruits of pepper plants

| Strain Number | Male parent | Female parent | Pro-Vitamin A* (βCarotene) | Vitamin C* | Vitamin E* |
|---|---|---|---|---|---|
| 8701 | VI-001 | VI-002 | 4.7 | 250 | 5.8 |
| 8703 | VI-003 | VI-004 | 3.4 | 250 | 5.7 |
| 8704 | VI-005 | VI-006 | 3.8 | 280 | 5.3 |

*Vitamin concentration- (mg/100 g FW)

These hybrid strains were obtained using the four parents' cross as described in Example 1. To select fruit which are non-pungent, the presence of a DNA marker for pungency was examined, as described in Example 2. The content of vitamin C, vitamin E, pro-vitamin A and total carotenoids was determined as described in Examples 3 and 4 detailed above. The male and female parent lines of strains 8701, 8703 and 8704 as indicated in Table 3, were obtained by successive steps of self-pollination and selection as described in the above Examples 1-5. The vitamin values shown in Table 3 are means of representative fruit picks. The vitamin content of the parental lines of 8701, 8703 and 8704 are presented in the Table 4:

TABLE 4

Vitamin content in parental lines of deposited pepper varieties (mg/ 100 g FW):

| Variety | M/F | Parent name | Vitamin A | Vitamin C | Vitamin E |
|---|---|---|---|---|---|
| 8701 | M | VI-001 | 6.47 | 385 | 7.11 |
| 8701 | F | VI-002 | 3.58 | 119 | 4.66 |
| 8703 | M | VI-003 | 3.61 | 430 | 5.6 |
| 8703 | F | VI-004 | 4.56 | 192 | 4.67 |
| 8704 | M | VI-005 | 2 | 432 | 6.51 |
| 8704 | F | VI-006 | 5 | 192 | 4.53 |

Hybrid pepper strains 8701, 8703 and 8704, seeds of which were deposited with NCIMB Ltd under accession numbers 41641, 41642 and 41643, respectively, and their parental lines, are characterized by non-pungent fruits with elevated vitamin content as shown in Tables 3 and 4. These strains are described herein as examples of plants producing fruit with elevated vitamin content according to the present invention, and is not meant to be limiting but is illustrative of various pepper types and lines that can be encompassed within the scope of the present invention.

TABLE 2

Vitamin content in fruit of pepper plants

| Strain | Vitamin C (mg/100 g FW) | Vitamin E (mg/100 g FW) | Pro-vitamin A (mg/100 g FW) | Carotenoids (mg/100 g FW) |
|---|---|---|---|---|
| A. Parent strains | | | | |
| Maor | 140.3 | 3.3 | 2.2 | 25.1 |
| E-8511 | 153.8 | 12.8 | 9.6 | 100.6 |
| CLR-7174 | 171.3 | 4.9 | 20.1 | 186.2 |
| C-8271 | 768.8 | 10.5 | 6.8 | 70.4 |
| B. $F_1$ plants | | | | |
| Maor × E-8511 | 192.5 | 5.2 | 5.2 | 45.8 |
| CLR-7174 × C-8271 | 350.1 | 4.0 | 7.1 | 69.3 |

| C. Representative Plant of the present invention | | | |
|---|---|---|---|
| Strain | Vitamin C (mg/100 g FW) | Vitamin E (mg/100 g FW) | Pro-vitamin A (mg/100 g FW) |
| ACE05F01-521 | 261 | 9.3 | 5.3 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials and steps for carrying out various disclosed functions may take a variety of alternative forms without departing from the invention.

The invention claimed is:

1. A pepper cultivar suitable for commercial growth having edible fruit of elevated vitamin content said fruit comprising a vitamin E content of at least 5 mg/100 g fresh weight, further comprising a pro-vitamin A content of at least 3 mg/100g fresh weight, or a vitamin C content of at least 200 mg/100g fresh weight or a combination thereof, wherein the genome of said cultivar is characterised by a deletion comprising the 700 bp marker sequence as set forth in SEQ ID NO: 3, and said deletion is cosegregated with a non pungency trait.

2. The pepper cultivar of claim 1, wherein the fruit are non-pungent and have a thick pericarp.

3. The pepper cultivar of claim 1, wherein the fruit comprises elevated levels of vitamin E of at least 5 mg/100 g fresh weight, pro-vitamin A of at least 3 mg/100 g fresh weight and vitamin C of at least 200 mg/100g fresh weight.

4. The pepper cultivar of claim 1, wherein the fruit further comprise at least 70 mg/100 g fresh weight of carotenoids.

5. The pepper cultivar of claim 1, wherein the cultivar is an inbred line or a hybrid.

6. The pollen of the cultivar of claim 1.

7. The ovule of the cultivar of claim 1.

8. The fruit of the cultivar of claim 1.

9. The seed of the cultivar of claim 1, wherein a cultivar grown from the seed produces edible fruit of elevated vitamin content said fruit comprising a vitamin E content of at least 5 mg/100 g fresh weight, further comprising a pro-vitamin A content of at least 3 mg/100g fresh weight, or a vitamin C content of at least 200 mg/100g fresh weight or a combination thereof, wherein the genome of said cultivar is characterised by a deletion comprising the 700 bp marker sequence as set forth in SEQ ID NO: 3, and said deletion is cosegregated with a non pungency trait.

10. The cultivar of claim 1 further comprising at least one additional trait selected from the group consisting of high germination rate, vigorous growth, herbicide resistance, insect resistance, resistance to bacterial, fungal or viral disease, and resistance to a non-biotic stress, wherein the additional trait is introduced by a method selected from the group consisting of breeding, single trait conversion and transformation.

11. The cultivar of claim 1 being a hybrid designated ACE05F01-521, seeds of which were deposited with NCIMB Ltd. under Accession No 41381.

12. A tissue culture of regenerable cells obtained from the pepper cultivar of claim 1 or a part thereof, the regenerable cells of said tissue culture are obtained from a plant part selected from the group consisting of leaves, pollen, embryos, roots, root tips, anthers, flowers, fruit and seeds.

13. The tissue culture of claim 12, wherein said tissue culture regenerates plants having edible fruit of elevated vitamin content said fruit comprising a vitamin E content of at least 5 mg/100 g fresh weight, further comprising a pro-vitamin A content of at least 3 mg/100g fresh weight, or an elevated vitamin C content of at least 200 mg/100g fresh weight or a combination thereof, wherein the genome of said plant is characterised by a deletion comprising the 700 bp marker sequence as set forth in SEQ ID NO: 3, and said deletion is cosegregated with a non pungency trait.

14. The tissue culture of claim 13, wherein the fruit are non-pungent and have a thick pericarp.

15. A pepper plant regenerated from the tissue culture of claim 12.

16. A method for producing a pepper plant having edible fruit of elevated vitamin content, said fruit comprising a vitamin E content of at least 5 mg/100 g fresh weight, further comprising a pro-vitamin A content of at least 3 mg/100g fresh weight, or a vitamin C content of at least 200 mg/100g fresh weight or a combination thereof, wherein the genome of said plant is characterised by a deletion comprising the 700 bp marker sequence as set forth in SEQ ID NO: 3, and said deletion is cosegregated with a non pungency trait said method comprising the steps of:
   a. selecting at least one pepper plant having fruit comprising an elevated vitamin E content, at least one pepper plant having fruit comprising an elevated pro-vitamin A content and at least one pepper plant having fruit comprising an elevated vitamin C content, as compared with edible fruit of currently available commercial pepper strains;
   b. crossing the at least one pepper plant having fruit comprising an elevated vitamin E content with a commercial pepper plant to produce a first $F_1$ population;
   c. crossing the at least one pepper plant having fruit comprising an elevated pro-vitamin A content with the at least one pepper plant having fruit comprising an elevated vitamin C content to produce a second $F_1$ population;
   d. crossing at least one plant from said first $F_1$ population with at least one plant from said second $F_1$ population to produce an $F_2$ population;
   e. examining a DNA sample obtained from the $F_2$ plants for the presence of a DNA sequence co-segregating with a high pungency trait, wherein the DNA sequence co-segregating with a high pungency trait comprises a polynucleotide sequence as set forth in SEQ ID NO:3 or a fragment thereof; and
   f. selecting plants lacking the DNA sequence set forth in SEQ ID NO:3 or fragments thereof with pepper fruit having vitamin E concentration of at least about 5 mg/100g fresh weight and at least one of pro-vitamin A concentration of at least about 3 mg/100g fresh weight and vitamin C concentration in the range of from about 200 mg to about 500 mg/100g fresh weight or a combination thereof.

17. The method of claim 16, further comprising the steps of:
   a. measuring the thickness of the pericarp in the fruit produced by the $F_2$ plants; and
   b. selecting plants having a thick pericarp.

18. The method of claim 17, further comprising the steps of selfing, at least once, the selected plants, and further selecting plants with pepper fruit having vitamin E concentration of at least about 5 mg/100g fresh weight and at least one of pro-vitamin A concentration of at least about 3 mg/100g fresh weight, vitamin C concentration of at least about 200 mg per 100g fresh weight and a combination thereof, wherein the fruit are non-pungent and have a thick pericarp.

19. The method of claim 16, wherein the fruit further comprise at least about 70 mg/100g fresh weight of carotenoids.

20. A method for producing a pepper plant having edible fruit of elevated vitamin content, said fruit comprising a vitamin E content of at least 5 mg/100 g fresh weight, further comprising a pro-vitamin A content of at least 3 mg/100g fresh weight, or a vitamin C content of at least 200 mg/100g fresh weight or a combination thereof, wherein the genome of said plant is characterised by a deletion comprising the 700 bp marker sequence as set forth in SEQ ID NO: 3, and said deletion is cosegregated with a non pungency trait said method comprising the steps of:
   a. selecting at least one pepper plant having fruit comprising an elevated vitamin E content, at least one pepper plant having fruit comprising an elevated pro-vitamin A content and at least one pepper plant having fruit comprising an elevated vitamin C content as compared to edible fruit of currently available commercial pepper strains;
   b. crossing each of the selected plants with a commercial pepper plant to produce at least one offspring population;

c. examining a DNA sample obtained from the offspring population for the presence of a DNA sequence co-segregating with a high pungency trait, wherein the DNA sequence co-segregating with a high pungency trait comprises a polynucleotide sequence as set forth in SEQ ID NO:3 or a fragment thereof; and;

d. selecting plants lacking the DNA sequence co-segregating with a high pungency trait with pepper fruit having vitamin E concentration of at least about 5 mg/100g fresh weight and at least one of pro-vitamin A concentration of at least about 3 mg/100g fresh weight; vitamin C concentration in the range of from about 200 mg to about 500 mg/100g fresh weight and a combination thereof, wherein the fruit are non-pungnt and having a thick pericarp.

21. The method of claim 20, wherein step (b) of crossing and step (d) of selecting are repeated at least once.

22. The method of claim 20, further comprising the steps of selfing, at least once, the selected plants, and further selecting plants with pepper fruit having vitamin E concentration of at least about 5 mg/100 g fresh weight and at least one of pro-vitamin A concentration of at least about 3 mg/100 g fresh weight, vitamin C concentration in the range of from about 200 mg to about 500 mg per 100 g fresh weight and a combination thereof, wherein the fruit are non-pungent and have a thick pericarp.

23. The method of claim 20, wherein the fruit further comprise at least about 70 mg/100 g fresh weight of carotenoids.

\* \* \* \* \*

SEQUENCE LISTING

<160> NUMBER OF SEQ ID NOS: 5

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1

```
gaccacgggt ctacggatag acctc                                          25

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
caaacctcgc cttcgtgaca atccca                                         26

<210> SEQ ID NO 3
<211> LENGTH: 731
<212> TYPE: DNA
<213> ORGANISM: Capsicum annuum

<400> SEQUENCE: 3
gaccacgggt ctacggatag acctcgggtc tacgaacaga ataggtcgc tgttcaaatc      60 aaaatgccaa ataactctt caaacaacta ttatcccacc attcaacact tcgttgctaa    120
ataaaccaca actaaaccaa acaccaaat tcgaagaaaa aatttctaca tcactacgaa    180
ttgattagca aaaaaaaaac gtttaaatgg atctagaaat gatcgaaact tgattttaac    240
taaccttgca aagcagcaac aacccttag tagctggaga agaagacgaa atgaaaatgg    300
catttttgga agaagtagtt tcaaaagcag gagttgggaa ttgaagagga gagagaggt    360 gggtttttt aaatattgga ataattggag ggtgttaggt gtattatt aaatttgtaa    420 agttgtaaaa atgatgaatt ggtcccttgg ccgatgcgtg ggccccactt tttcataaaa    480
aataaatcaa aaagaaatta agtaggtatt tgacaaatta attttggagg gttccttctt    540
tgccaattat tccccactaa gctactccca ttcactctta tattatagat tatagtataa    600
agtaatacaa actatgaatt gttttttatat tttattttac aagttatgaa tagtgtttat    660
ataggtctct atttccatac aatcacattt tgtgggcagt ttttttggga ttgtcacgaa    720
ggcgaggttt g                                                         731

<210> SEQ ID NO 4
<211> LENGTH: 3752
<212> TYPE: DNA
<213> ORGANISM: Capsicum annuum

<400> SEQUENCE: 4
tcattagaag gtcataccgc tccacgaaaa tgcaccttga agatataac acggacaacg      60 aatcattatc cccatcatca ctattactcc cacttccctt gcactcttca ctgtcaccac    120
tgacactccg cttggcaaca ttttcactat aatcgacgta gtcgcttatc tcctttaact    180
ccgaatctga ttcggacacc gactcttcag ttttctttct ttttgacact ttttcaactg    240
tcgcagctct tcttttttcta ctactaccag cggtatcgtc tttctttta ggaatgataa    300 atttttctacc catttttcaac acaatctaca cctaaagaac aaacatccca ttttcagttc    360
atagacgaca agtctatcaa cagaaataac ttaatgatca aatgaacacc accccccccc    420 ccccaaaaa aaaaaaatta acaaacaccc catcattaaa cagttcacta cacaaacata    480
caataattga atcaaatcaa acatgcaaaa tatcaaaaca caacaattgc taaaaatcaa    540
actagtgcac ctaatcaaac taattagcta ttaaatattc aattctcact attttaacaa    600 tcatgttttta aagaatttc atacgtctga aaattgaaat atatctaggg cattctcatt    660
```

```
tcatagacca cgggtctacg gatagacctc gggtctacga acagaaatag gtcgctgttc    720
aaatcaaaat gccaaaataa ctcttcaaac aactattatc ccaccattca acacttcgtt    780
gctaaataaa ccacaactaa accaaaacac caaattcgaa gaaaaaattt ctacatcact    840
acgaattgat tagcaaaaaa aaaacgttta aatggatcta gaaatgatcg aaacttgatt    900
ttaactaacc ttgcaaagca gcaacaaccc cttagtagct ggagaagaag acgaaatgaa    960
aatggcattt ttggaagaag tagtttcaaa agcaggagtt gggaattgaa gaggagagag   1020
agggtgggtt ttttttaaata ttggaataat tggagggtgt taggtgtatt atattaaatt   1080
tgtaaagttg taaaaatgat gaattggtcc cttggccgat gcgtgggccc cacttttttca   1140 taaaaaataa atcaaaaaga aattaagtag gtatttgaca aattaattttt ggagggttcc   1200 ttctttgcca attattcccc actaagctac tcccattcac tcttatatta tagattatag   1260
tataaagtaa tacaaactat gaattgtttt tatattttat tttacaagtt atgaatagtg   1320
tttatatagg tctctatttc catacaatca cattttgtgg gcagtttttt tgggattgtc   1380
acgaaggcga ggtttgttca ttttgtggaa agagaattgg atttctacat ttttatcatc   1440
ttctaggtgt gatgttgata ctactatttg cccaaatatt tgttttaaac atattaatat   1500
tatgtatcaa aatgtgtaca atataattta acacacgtgc agtatgcatg tatcgcgaaa   1560
ctagttaatt acatgcatca catgtaatag caatagtatt attgtacgac gtactaatat   1620
attagtatct attctagcta ctaatttcct cttaaccgtc tccatgctga aaacaacgcc   1680
acagtgcaac gagccttcta taaaagttga attatataaa aataaggtac agtttagaaa   1740
taaaactaac aaaaaggtaa cctatagttt gggggttggg tagaggttgt ttagccagta   1800
actctattat ttcatttcct tttgtctata taagtgtatc catatatgca agaaaatgtc   1860
aaccggccag cagcatatat ttatttgtta aattaattat ggcttttgca ttaccatcat   1920
cacttgtttc agtttgtaac aaatctttta tcaaaccttc ctctctcacc ccctctacac   1980
ttagatttca caagctatct ttcatcgatc aatctttaag taatatgtat atcccttgtg   2040 catttttta ccctaaagta caacaaagac tagaagactc caaaaattct gatgagcttt    2100
cccatatagc ccacttgcta caaacatctc tatcacaaac tctagtctct tactatcctt   2160
atgctggaaa gttgaaggac aatgctactg ttgactgtaa cgatatggga gctgagttct   2220
tgagtgttcg aataaaatgt tccatgtctg aaattcttga tcatcctcat gcatctcttg   2280
cagagagcat agttttgccc aaggatttgc cttgggcgaa taattgtgaa ggtggtaatt   2340
tgcttgtagt tcaagtaagt aagtttgatt gtggggggaat agccatcagt gtatgctttt   2400
cgcacaagat tggtgatggt tgctctctgc ttaatttcct taatgattgg tctagcgtta   2460
ctcgtgatca tacgacaaca actttagttc catctcctag atttgtagga gattcagtct   2520
tctctacaca aaaatatggt tctctcatta cgccacaaat tttgtccgat ctcaaccagt   2580
gcgtacagaa aagactcatt tttcctacag ataagttaga tgcacttcga gctaaggtaa   2640
tactaccatc gtccattatt gtttgtctta cggtattttt gaaagaata atatttaata   2700 gtcttcttga gacatatttc acttaacaag cctaggctat ttagtctatt tgtagaagct   2760
actcttaaac gcctcactta gttaatagca ctccacttat tggtgtcaaa aactactctt   2820
ggacatgtca tttacttaat aacactccac ttaattatcg aacagtaaag tggaaaatat   2880
aaaagaatgc agtaataaat acttgtagtt tttccgaaat gaaaagtact gaataattat   2940
tttaaaataa atttagtttg gttgacatta atttgggatt gaaggtggca gaagaatcag   3000
gagtaaaaaa tccaacaagg gctgaagttg ttagcgctct tcttttcaaa tgtgcaacaa   3060
```

-continued

```
aggcatcatc atcaatgcta ccatcaaagt tggttcactt cttaaacata cgtactatga    3120
tcaaacctcg tctaccacga aatgccattg gaaatctctc gtctattttc tccatagaag    3180
caactaacat gcaggacatg gagttgccaa cgttggttcg taatttaagg aaggaagttg    3240
aggtggcata caagaaagac caagtcgaac aaaatgaact gatcctagaa gtagtagaat    3300
caatgagaga agggaaactg ccatttgaaa atatggatgg ctataagaat gtgtatactt    3360
gcagcaatct ttgcaaatat ccatactaca ctgtagattt tggatgggga agacctgaaa    3420
gggtgtgtct aggaaatggt ccctccaaga atgccttctt cttgaaagat tacaaagctg    3480
ggcaaggcgt ggaggcgcgg gtgatgttgc acaagcaaca aatgtctgaa tttgaacgca    3540
atgaggaact cgttgagttc attgcctaat taattccaag ttttggagta attggatgtc    3600
atttccaagt cttttgtggt gtttgattga agagagaggg attttacgaa ataaaggaat    3660
acttttgaaa cttacgaaac aaaggtagga atactttgt aattgttgtg tgtttcatca     3720
acataattac aacggaagtt tacggtcaac aa                                  3752

<210> SEQ ID NO 5
<211> LENGTH: 1190
<212> TYPE: DNA
<213> ORGANISM: Capsicum annuum

<400> SEQUENCE: 5
tcattagaag gtcataccgc tccacggaaa agactcattt ttcctacaga taagttagat      60
gcacttcgag ctaaggtaat actaccatcg tccattattg tttgtcttac ggtattttg    120 aaaagaataa tatttaatag tcttcttgag acatatttca cttaacaagc ctaggctatt    180
tagtctattt gtagaagcta ctcttaaacg cctcacttag ttaatagcac tccacttatt    240
ggtgtcaaaa actactcttg gacatgtcat ttacttaata acactccact taattatcga    300
acagtaaagt ggaaaatata aagaatgca gtaataaata cttgtagttt ttccgaaatg     360
aaaagtactg aataattatt ttaaaataaa tttagtttgg ttgacattaa tttgggattg    420
aaggtggcag aagaatcagg agtaaaaaat ccaacaaggg ctgaagttgt tagcgctctt    480
cttttcaaat gtgcaacaaa ggcatcatca tcaatgctac catcaaagtt ggttcacttc    540
ttaaacatac gtactatgat caaacctcgt ctaccacgaa atgccattgg aaatctctcg    600
tctattttct ccatagaagc aactaacatg caggacatgg agttgccaac gttggttcgt    660
aatttaagga aggaagttga ggtggcatac aagaaagacc aagtcgaaca aaatgaactg    720
atcctagaag tagtagaatc aatgagagaa gggaaactgc catttgaaaa tatggatggc    780
tataagaatg tgtatacttg cagcaatctt tgcaaatatc catactacac tgtagatttt    840
ggatggggaa gacctgaaag ggtgtgtcta ggaaatggtc cctccaagaa tgccttcttc    900
ttgaaagatt acaaagctgg gcaaggcgtg gaggcgcggg tgatgttgca caagcaacaa    960
atgtctgaat ttgaacgcaa tgaggaactc gttgagttca ttgcctaatt aattccaagt   1020
tttggagtaa ttggatgtca tttccaagtc ttttgtggtg tttgattgaa gagagaggga   1080
ttttacgaaa taaggaata cttttgaaac ttacgaaaca aaggtaggaa taatttgtaa    1140
ttgttgtgtg tttcatcaac ataattacaa cggaagttta cggtcaacaa              1190
```